United States Patent [19]

Crawford et al.

[11] 4,425,275

[45] Jan. 10, 1984

[54] PROCESS FOR SEPARATING 3-HYDROXY STEROIDS OR STEROLS FROM MIXTURES SUCH AS LIPIDS

[75] Inventors: Richard R. Crawford, Pittsford; William P. Blum, Rochester; David C. Naramore, Pittsford, all of N.Y.

[73] Assignee: Eastman Kodak Company, Rochester, N.Y.

[21] Appl. No.: 397,313

[22] Filed: Jul. 12, 1982

[51] Int. Cl.$^3$ ............................................... C07J 9/00
[52] U.S. Cl. ............................................... 260/397.25
[58] Field of Search .................................. 260/397.25

[56] References Cited

U.S. PATENT DOCUMENTS 4,057,541  11/1977  Weber et al. .................... 260/397.25
4,279,828  7/1981  Foster ............................. 260/397.25

*Primary Examiner*—Elbert L. Roberts
*Attorney, Agent, or Firm*—Clyde L. Tootle; Daniel B. Reece, III

[57] ABSTRACT

A process for separating 3-hydroxy steroids from sterol concentrate mixtures by combining a solution of the sterol-containing mixture in a cosolvent of a dialkyl ketone and a low molecular weight alcohol with a slurry or solution of calcium bromide. The complexed sterols are isolated by filtration and the sterols can be subsequently liberated from the complex by treatment with an aqueous/alcohol and isolated by filtration and drying. The complexed sterols are of large particle size which allows rapid filtration.

9 Claims, No Drawings

PROCESS FOR SEPARATING 3-HYDROXY STEROIDS OR STEROLS FROM MIXTURES SUCH AS LIPIDS

DESCRIPTION

The present invention relates to a process for separating sterols from sterol concentrate mixtures.

Various processes are known in the art for separating sterols such as 3-hydroxy steroids from mixtures of such sterols and other components such as lipids. One such mixture is phytosterols in soybean oil deodorizer distillate. The separation of the 3-hydroxy steroids from such mixtures is important because these 3-hydroxy steroids are useful as raw materials for production of steroid drugs such as hydrocortisone. One such known process is described in German Pat. No. 827,199 wherein the mixture is dissolved, preferably in a hydrocarbon solvent, and is heated with a four- to sixteen-fold excess of anhydrous zinc chloride. After cooling of the solution, the precipitated ZnCl-sterol adduct can be separated out and the complex separated into the individual components. Another such known process as set forth in British Pat. No. 1,164,769 describes a method for the isolation of sterols from mixtures wherein the mixture is dissolved, preferably in a hydrocarbon solvent, the solution is mixed with an aqueous solution of a metal salt which is suitable for complex formation, the water is progressively removed by azeotropic distillation, and the precipitated adduct is isolated and the sterol recovered in a conventional manner after cooling of the mixture.

Such known methods have the disadvantage that they are technically very costly on account of the high reaction temperature (customarily over 100° C.) and that in the isolation of many 3-hydroxy steroids and 3-oxo steroids considerable loss of product is experienced, since these steroids can be destroyed under these conditions. In addition, these known methods often have the disadvantage that the recovery of the metal salt used for formation of the adduct, which is necessary in a method carried out on large scale simply with regard to environmental considerations, is often very costly.

Another prior art process for separating 3-hydroxysteroids from mixtures of such steroids and lipids as disclosed in U.S. Pat. No. 4,057,541 is carried out by forming a solution of a mixture of one or more 3-hydroxy steroids and lipids in methyl isobutyl ketone or methyl n-amyl ketone, or mixtures thereof, which is mixed with calcium bromide or a solution of calcium bromide in methyl isobutyl ketone or methyl n-amyl ketone, or mixtures thereof, and the precipitated sterol complex separated and recovered in a known manner. However, in this process the sterol bromide complex which forms precipates out in very small particles which requires long filtration times. It would therefore be a significant advance in the state of the art to provide a relatively simple process useful commercially which provides excellent separation and requires short filtration times to separate 3-hyroxy steroids from mixtures of sterols concentrate.

In accordance with the present invention, a process is provided for isolating 3-hydroxy steroids from sterols concentrates by merely combining a solution of the sterol-containing mixture in a cosolvent of a dialkyl ketone and a low molecular weight alcohol with a slurry or solution of calcium dibromide. The resulting mixture can then be stirred or agitated at ambient temperature for a suitable period to form the sterol-$CaBr_2$ complex. The sterol-$CaBr_2$ complex precipitates out in large particles which can be easily and quickly isolated by filtration. The sterols are then liberated from the sterol-$CaBr_2$ complex by treatment with an aqueous alcoholic wash and isolated by filtration.

The cosolvent used in the present invention is a mixture of a dialkyl ketone and a low molecular weight alcohol. The dialkyl ketone preferably has about 5 to 6 carbon atoms. Such dialkyl ketones are preferably methylisobutyl ketone and methylisoamyl ketone. The low molecular weight alcohols are preferably methyl alcohol, ethyl alcohol and isopropyl alcohol. The cosolvent contains about 1 to 5 parts alcohol per 100 parts ketone, preferably 2 to 4 parts alcohol per 100 parts ketone. If the cosolvent contains less than one part alcohol the particle size of the complex precipitate is decreased so that the filtration time is not considerably decreased. Amounts greater than 5 parts do not appreciably increase the particle size and decrease the yield of complex.

The process of this invention is carried out by dissolving the sterol containing concentrate in the cosolvent. About 100 parts of sterol concentrate can be dissolved in about 30 to 150 parts of dialkyl ketone having about 5 to 6 carbon atoms and about 0.8 to 6 parts of a low molecular weight alcohol. About 15 parts calcium bromide can be dissolved in about 30 to 150 parts of the ketone used in preparing the cosolvent. The two solutions are mixed, preferably at ambient temperature for a period of 1 to 60 minutes, preferably 5 to 15 minutes. The sterol complex precipitates out in large particles and the slurry is filtered and washed. The sterol can be recovered from the complex by processes well known in the art such as for example by slurrying in methanol or water followed by filtration and drying.

The amount of cosolvent used depends on the solubility of the sterol-lipid concentrate. The amount of calcium dibromide used depends on the concentration of the sterols in the sterol concentrate. The greater the amount of sterol present, the greater the amount calcium dibromide necessary to provide sufficient $CaBr_2$ to form complexes with the sterols.

The solvent used to wash the filtered sterol-complex obtained after removal of the solvent or diluents can be any suitable solvent which does not dissolve the complex. Such solvents include heptane, hexane, toluene, cyclohexane, methyl ethyl ketone, methyl isobutyl ketone and the like.

It should be noted that heat may be used to dissolve the sterol concentrate in the cosolvent and during complex formation, but is not necessary.

This invention can be further illustrated by the following examples, although it will be understood that these examples are included merely for purposes of illustration and are not intended to limit the scope of the invention unless otherwise specifically indicated.

EXAMPLE 1

About 200 grams of sterol concentrate containing 22% sterols is dissolved in 150 ml of methyl isobutyl ketone. About 30 grams of calcium bromide dihydrate is dissolved in 250 ml methyl isobutyl ketone. The two solutions are mixed and intimately mixed at ambient temperature, about 25° C., for a period of one hour. The slurry was filtered which required nine minutes.

Repeating this procedure using 200 grams of sterol concentrate containing 16% sterols required a filtration time of 15 minutes.

EXAMPLE 2

About 200 grams of sterol concentrate containing 22% sterols is dissolved in a mixture of 200 ml methyl isobutyl ketone and 6.3 ml methanol. About 30 grams of calcium bromide dihydrate is dissolved in 200 ml of methyl isobutyl ketone. The solutions were mixed and reacted at ambient temperature for one hour. The slurry was filtered which required 3.7 minutes.

Repeating this procedure using 200 grams of sterol concentrate containing 16% sterols required a filtration time of only 4.5 minutes and 29.8 grams sterol complex was recovered.

EXAMPLE 3

About 200 grams of sterol concentrate containing 16% sterols is dissolved in 200 ml methyl isobutyl ketone. About 30 grams of calcium bromide dihydrate is dissolved in 200 ml of methyl isobutyl ketone and 6.3 ml methanol. The two solutions are mixed and reacted according to the procedure of Example 2. After reaction the slurry was filtered which required 17 minutes. This example shows that the solvent used to dissolve the sterol concentrate must contain the low molecular weight alcohol.

EXAMPLE 4

About 200 grams of sterol concentrate containing 16% sterols is dissolved in 200 ml methyl isobutyl ketone and 3.15 ml. methanol. About 30 grams of calcium bromide dihydrate is dissolved in 200 ml of methyl isobutyl ketone. The two solutions are mixed and reacted according to the procedure of Example 2. After reaction the slurry was filtered which required only 5.8 minutes and 29.2 grams sterol complex recovered.

EXAMPLE 5

About 200 grams of sterol concentrate containing 16% sterols is dissolved in 200 ml methyl isobutyl ketone and 12.6 ml. methanol. About 30 grams of calcium bromide dihydrate is dissolved in 200 ml of methyl isobutyl ketone. The two solutions are mixed and reacted according to the procedure of Example 2. After reaction the slurry was filtered which required only 3.3 minutes and only 21.2 grams sterol complex recovered.

EXAMPLE 6

About 200 grams of sterol concentrate containing 22% sterols is dissolved in 150 ml of methyl isoamyl ketone. About 30 grams of calcium bromide dihydrate is dissolved in 250 ml methyl isoamyl ketone. The two solutions are mixed and intimately mixed at ambient temperature, about 25° C., for a period of one hour. The slurry was filtered which required 18.5 minutes.

EXAMPLE 7

The procedure of Example 6 was repeated except that 6.3 ml of methanol as cosolvent was added to the methyl isoamyl ketone used to dissolve the sterol concentrate. Filtration time was only 3.5 minutes.

EXAMPLE 8

About 200 grams of sterol concentrate containing 20% sterols is dissolved in 200 ml of methyl isobutyl ketone. About 30 grams of calcium bromide dihydrate is dissolved in 200 ml methyl isobutyl ketone. The two solutions are mixed and intimately mixed at ambient temperature, about 25° C., for a period of one hour. The slurry was filtered which required 10.8 minutes.

EXAMPLE 9

The procedure of Example 8 is repeated except that 6.3 ml methanol as cosolvent was added to the methyl isobutyl ketone used to dissolve the sterol concentrate. Filtration required only 4.5 minutes.

EXAMPLE 10

The procedure of Example 9 is repeated except that 6.3 ml of ethanol replaces the 6.3 ml of methanol in the cosolvent. Filtration time was only 3 minutes.

EXAMPLE 11

The procedure of Example 10 is repeated except that 6.3 ml of isopropanol replaces the 6.4 ml of ethanol in the cosolvent. Filtration time was only 3 minutes.

EXAMPLE 12

About 200 grams of sterol concentrate containing 20% sterols is dissolved in 200 ml methyl isobutyl ketone and 6.3 ml methanol. About 30 grams of calcium bromide dihydrate is dissolved in 200 ml of methyl isobutyl ketone. The two solutions are mixed and reacted at ambient temperature for 15 minutes and filtered which required only 1 minute and gave a yield of 37.9 grams sterol complex.

EXAMPLE 13

The procedure of Example 12 was repeated except that the two solutions were mixed and stirred and filtered after only 1 minute reaction time. The filtration required only 30 seconds and 37.8 grams sterol complex recovered.

The process of the present invention provides an improved process for separating 3-hydroxy steroids from sterol concentrates. Further, the 3-hydroxy steroids can be used to provide starting materials for preparation of valuable steroids.

The invention has been described in detail with particular reference to preferred embodiments thereof, but it will be understood that variations and modifications can be effected within the spirit and scope of the invention.

I claim:

1. A method for separating sterols from sterol containing natural source which comprises (1) dissolving said sterol containing natural source in a mixture of a dialkyl ketone having about 5 or 6 carbons and a lower aliphatic alcohol, (2) adding to the mixture containing dissolved sterols a calcium bromide solution containing sufficient calcium bromide to complex with said sterols, (3) mixing the resulting dissolved sterols and calcium bromide solution for a period to effect reaction therebetween, and (4) thereafter recovering the resultant solid sterol complex.

2. A method for separating sterols from sterol containing natural source according to claim 1 wherein said dialkyl ketone is at least one member of the group consisting of methylisobutyl ketone and methylisoamyl ketone.

3. A method for separating sterols from sterol containing natural source according to claim 2 wherein said lower aliphatic alcohol is at least one member selected from the group consisting of methyl alcohol, ethyl alcohol and isopropyl alcohol.

4. A method for separating sterols from sterol containing natural source according to claim 3 wherein said lower aliphatic alcohol is present in an amount of from about 0.5% to about 1.5%, by weight, of the total liquid employed in the separation.

5. A method for separating sterols from sterol containing natural source according to claim 4 wherein said lower aliphatic alcohol is present in an amount of about 1.0%, by weight, of the total liquid employed in the separation.

6. A method for separating sterols from sterol containing natural source which comprises (1) dissolving in an amount of about 100 parts of said sterol containing natural source in a mixture of about 30 parts to about 150 parts of a dialkyl ketone having about 5 or 6 carbons and about 0.8 to about 6 parts of a lower aliphatic alcohol, (2) adding to the mixture containing dissolved sterols about 15 parts of a calcium bromide solution in about 30 to about 150 parts of dialkyl ketone having about 5 or 6 carbon atoms, (3) mixing the resulting dissolved sterols and calcium bromide solution for a period of about 1 to about 60 minutes, and (4) thereafter recovering the resultant solid sterol complex.

7. A method for separating sterols from sterol containing natural source according to claim 6 wherein said dialkyl ketones are at least one member of the group consisting of methylisobutyl ketone and methylisoamyl ketone.

8. A method for separating sterols from sterol containing natural source according to claim 7 wherein said lower aliphatic alcohol is at least one member selected from the group consisting of methyl alcohol, ethyl alcohol and isopropyl alcohol.

9. A method for separating sterols from sterol containing natural source according to claim 8 wherein said lower aliphatic alcohol is present in an amount of from about 1.0%, by weight, of the total liquid employed in the separation.

* * * * *